US010584368B2

(12) United States Patent
Yampol'skiy et al.

(10) Patent No.: US 10,584,368 B2
(45) Date of Patent: Mar. 10, 2020

(54) METHOD AND AGENTS FOR DETECTING LUCIFERASE ACTIVITY

(71) Applicant: OBSCHESTVO S OGRANICHENNOY OTVETSTVENNOSTYU "PLANTA", Moscow (RU)

(72) Inventors: Il'ya Viktorovich Yampol'skiy, Moscow (RU); Valentin Nikolaevich Petushkov, Krasnoyarsk (RU); Konstantin Viktorovich Purtov, Krasnoyarsk (RU); Natal'ya Sergeevna Rodionova, Krasnoyarsk (RU); Mikhail Sergeevich Baranov, Moscow (RU)

(73) Assignee: OBSCHESTVO S OGRANICHENNOY OTVETSTVENNOSTYU "PLANTA", Moscow (RU)

( * ) Notice: Subject to any disclaimer, the term of this patent is extended or adjusted under 35 U.S.C. 154(b) by 68 days.

(21) Appl. No.: 15/553,411

(22) PCT Filed: Apr. 21, 2016

(86) PCT No.: PCT/RU2016/000229
§ 371 (c)(1),
(2) Date: Aug. 24, 2017

(87) PCT Pub. No.: WO2016/144212
PCT Pub. Date: Sep. 15, 2016

(65) Prior Publication Data
US 2018/0163248 A1 Jun. 14, 2018

(30) Foreign Application Priority Data
Feb. 25, 2015 (RU) .................................. 2015106305

(51) Int. Cl.
*C12Q 1/26* (2006.01)
*C07D 307/62* (2006.01)
*C12Q 1/66* (2006.01)

(52) U.S. Cl.
CPC ............. *C12Q 1/26* (2013.01); *C07D 307/62* (2013.01); *C12Q 1/66* (2013.01); *G01N 2333/90241* (2013.01); *G01N 2333/90248* (2013.01)

(58) Field of Classification Search
None
See application file for complete search history.

(56) References Cited

U.S. PATENT DOCUMENTS

| 2002/0086424 A1* | 7/2002 | Contag | C12N 9/0069 435/400 |
| 2002/0192755 A1* | 12/2002 | Francis | C12N 15/74 435/69.1 |
| 2004/0063165 A1* | 4/2004 | Gawad | C12Q 1/66 435/8 |
| 2014/0272970 A1* | 9/2014 | Zegzouti | C12Q 1/66 435/6.11 |

FOREIGN PATENT DOCUMENTS

WO   WO 2012/086889   6/2012

OTHER PUBLICATIONS

Baldwin, Structure, 4(3):223-228 (1996).*
Spaans et al., Front. Microbiol., 6(742):1-27 (2015).*
Tsarkova et al., Acc. Chem. Res., 49:2372-2380 (2016).*
Welsh et al (Meth. Enzymol. 393(11):269-287 (2005).*
Oliveira, A.G., et al; "The enzymatic nature of fungal bioluminescence"; *Photochemical & Photobiological Sciences*, An International Journal; vol. 8, No. 10, pp. 1349-1488 (2009).
Lee, In-Kyoung, et al; "Styrylpyrone-class compounds from medicinal fungi *Phellinus* and *Inontus* spp., and their medicinal importance"; *The Journal of Antiobiotics*, vol. 64, pp. 349-359 (2011).
Beckert, C., et al; "Styrylpyrone Biosynthesis in *Equisetum arvense*"; *Phytochemistry*, vol. 44, No. 2, pp. 275-283 (1997).
Newman, S., et al; "Preparation of cDNA Libraries and Isolation and Analysis of Specific Clones"; pp. 13-48 (1990).
Michael R. Green and Joseph Sambrook; "Molecular Cloning—A Laboratory Manual"; Fourth Edition, vol. 1, 34pgs. (2012).
Barany, Francis; "Single-stranded hexameric linkers: a system for in-phase insertion mutagenesis and protein engineering"; *Gene*, vol. 37, pp. 111-123 (1985).
Colicelli, J., et al; "A temperature-sensitive mutation constructed by "linker insertion" mutagenesis"; *Mol. Gen Genet*, vol. 199, pp. 537-539 (1985).
Oba, Yuichi, et al; "Identification of hispidin as a bioluminescent active compound and its recycling biosynthesis in the luminous fungal fruiting body"; *Photochemical & Photobiological Sciences*; Royal Society of Chemistry, 6 pages (2017).
Kaskova, Z.M., et al; "Mechanism and color modulation of fungal bioluminescence"; *Science Advances, Research Article*; 9 pages; 3:e1602847 (2017).
Purtov, K.V., et al; "The Chemical Basis of Fungal Bioluminescence**"; *Angew. Chem. Int. Ed.*; 54, pp. 8124-8128 (2015).
Teranishi, Katsunori; "Inhibition of bioluminescence in the living gills of the luminous fungus *Mycena chlorophos* by trans-4-aminocinnamic acid"; *Biochemical and Biophysical Research Communications*; pp. 1-5 (2017).
Teranishi, Katsunori; "A combination of NADHP and hispidin is not essential for bioluminescence in luminous fungal living gills of *Mycena chlorophos*"; *Wiley Luminescence*, The Journal of Biological and Chemical Luminescence; pp. 1-7 (2017).

(Continued)

*Primary Examiner* — Thomas J. Visone
(74) *Attorney, Agent, or Firm* — Nixon & Vanderhye P.C.

(57) ABSTRACT

The invention provides methods and reagents for detecting luciferase in biological samples. The methods and reagents of the present invention allow detecting fungal luciferase or a functional analog thereof.

11 Claims, 10 Drawing Sheets

(56) References Cited

OTHER PUBLICATIONS

Teranishi, Katsunori; "Second bioluminescence-activating component in the luminous fungus *Mycena chlorophos*"; *Luminescence, The Journal of Biological and Chemical Luminescence*; pp. 1-8 (2016).

Teranishi, Katsunori; Identification of possible light emitters in the gills of a bioluminescent fungus *Mycena chlorophos*; *Luminescence, The Journal of Biological and Chemical Luminescence*; pp. 1-7 (2016).

Teranishi, Katsunori; "Localization of the bioluminescence system in the pileus of *Mycena chlorophos*"; *Luminescence*, The Journal of Biological and Chemical Luminescence; 31:594-599 (2016).

Tsuji, et al; *Photochem Photobiol*, 62(4):657-661 (1995).

Oliveira et al, *Photochemical & Photobiological Sciences*, 11(2) (2012).

International Search Report issued in PCT/RU2016/000229 dated Oct. 6, 2016.

Abstract of Airth et al., "The isolation of catalytic components required for cell-free fungal bioluminescence" *Archives of Biochemistry and Biophysics*, vol. 97, iss. 3: 567-573 (Jun. 1962).

Abstract of Petushkov et al., "A Novel Type of Luciferin from the Siberian Luminous Earthworm *Fridericia heliota*: Structure Elucidation by Spectral Studies and Total Synthesis" *Angewandte Chemie*, vol. 126, iss. 22: 5672-5674 (May 26, 2014).

Airth et al., "Light Emission from Extracts of Luminous Fungi" *Notes*, vol. 77: 249-250 (1958).

Cormier et al., "The enzymology and Molecular Biology of the $Ca^{2+}$-Activated Photoprotein, Aequorin" *Photochemistry and Photobiology*, vol. 49, No. 4: 509-512 (1989).

Endo et al., "Fluorescent Constituents and Cultivation of *Lampteromyces japonicas*" *Chemical Communications*, pp. 309-310 (1970).

Hayashi et al., "Extraction and purification of a luminiferous substance from the luminous mushroom *Mycena chlorophos*" *Biophysics*, vol. 8: 111-114 (2012), DOI: 10.2142/biophysics.8.111.

Isobe et al., "Lampteromyces Bioluminescence—1. Identification of Riboflavin as the Light Emitter in the Mushroom, *L. japonicas*" *Journal of Bioluminescene and Chemiluminescence*, vol. 1: 181-188 (1987).

Isobe et al., "Lampteromyces Bioluminescence—2 Lampteroflavin, a Light Emitter in the Luminous Mushroom, *L. japonicas*" *Tetrahedron Letters*, vol. 29, No. 10: 1169-1172 (1988).

Nakamura et al. "Panal: A Possible Precursor of Fungal Luciferin" *Tetrahedron*, vol. 44, No. 6: 1597-1602 (1988).

Oliveira et al., "Evidence that a single bioluminescent system is shared by all known bioluminescent fungal lineages" *Photochemical & Photobiological Sciences*, vol. 11, No. 5: 848-852 (2012), DOI: 10.1039/c2pp25032b.

Prasher et al., "Sequence Comparisons of Complementary DNAs Encoding Aequorin Isotypes" *Biochemistry*, vol. 26: 1326-1332 (1987).

Shimomura et al., "Structure and Non-Enzymatic Light Emission of Two Luciferin Precursors Isolated from the Luminous Mushroom *Panellus stipticus*" *Journal of Bioluminescence and Chemiluminescence*, vol. 8: 201-205 (1993).

Shimomura, *Bioluminescence: Chemical Principles and Methods*, Chapter 9 Luminous Fungi (pp. 266-300), World Scientific Publishing Co. Pte. Ltd., Singapore (2006).

Stevani et al., "Current Status of Research on Fungal Bioluminescence: Biochemistry and Prospects for Ecotoxicological Application" *Photochemistry and Photobiology*, vol. 89: 1318-1326 (2013), DOI: 10.1111/php.12135.

Tsuji et al., "Molecular Evolution of the $Ca^{2+}$-Binding Photoproteins of the Hydrozoa" *Photochemistry and Photobiology*, vol. 62, No. 4: 657-661 (1995).

\* cited by examiner

METHOD AND AGENTS FOR DETECTING LUCIFERASE ACTIVITY

This application is the U.S. national phase of International Application No. PCT/RU2016/000229 filed Apr. 21, 2016 which designated the U.S. and claims priority to Russian Patent Application No. 2015106305 filed Feb. 25, 2015, the entire contents of each of which are hereby incorporated by reference.

FIELD OF THE INVENTION

The present invention relates to the field of biology and chemistry and more particularly to the bioluminescent systems.

BACKGROUND OF THE INVENTION

Biouminescence is a process wherein living organisms emit light in the course of a biochemical reaction wherein chemical energy transforms into light energy. Several types of bioluminescent systems have been described.

For example, the systems of a number of marine coelenterates comprising aequorin proteins have been described (Prasher, et al., Biochem. 1987, 26:1326-1332; Tsuji et al., Photochem Photobiol, 1995 62(4):657-661). The aequorin family also comprises obelin, halistaurin (mitrocomin), phiallidin (clytin), etc. These are photoproteins comprising luciferin which is covalently bound thereto. In the presence of Ca2+ ions, luciferin undergoes chemical changes resulting in the formation of a product in an excited state.

The components of the bioluminescent systems (luciferases, photoproteins, luciferins, etc.) are commonly used reagents in a plurality of assays including diagnostic systems, quality control systems, etc. For example, aequorin and its homologs are commonly used in studying the release and fixation of Ca2+ in biological systems; for example, during a muscle contraction. For example, the use of the bioluminescent systems has been described in detail in Cormier, M. L. et al., Photochem. & Photobiol. 49/4, 509-512 (1989), Smith, D. F. et al. in "Bioluminescence and Chemiluminescence: Current Status (P. Stanley & L. Krick, eds.), John Wiley and Sons, Chichester, U.K. 1991, 529-532.

The discovery of the new components of bioluminescent systems makes it possible to broaden the spectrum of available assays and applications.

Bioluminescence of higher fungi is commonly known. The fruiting bodies of many fungi are capable of producing constant light which can be clearly seen by an unaided eye. Luminescence of the extracts of bioluminescent fungi was first demonstrated in 1959 (R. L. Airth and W. D. McElroy, Light emission from extracts of luminous fungi, J. Bacteriol., 1959, 77, 249). Light was produced in response to adding NADPH to the mixture of "cold" and "hot" extracts made of fungal mycelia of *Collybia velutipes* and *Armillaria mellea*.

As used herein, the term "cold extract" refers to an extract comprising the enzymes of the fungal bioluminescent system and free from low-molecular-weight components of the system. In order to obtain the cold extract, the following protocol may be used: wash the biomass of fungal mycelium to get rid of culture medium, then put the biomass into sufficient amount of distilled water (1:100-1:200 by mass) for 15-16 hours at the temperature of 26° C. After steeping, collect the biomass and freeze at −20° C. Then, thaw the biomass and rinse with distilled water a few times. Pour 0.01 M phosphate buffer (pH 7.5) over the mycelium with a mass to volume ratio of 1:10. Then, using a homogenizer, grind and ultrasound (for example, using Ultrasonic disintegrator UD-20 (Techpan, Poland) or a similar device) on ice 5 times for 1 minute in 1 minute intervals. Centrifugate the obtained homogenate at 30000 g for 20 minutes at 4° C.

As used herein, the term "hot extract" refers to an extract comprising the low-molecular-weight components of the system and free from the enzymes of the fungal bioluminescent system. In order to obtain a hot extract, the following protocol may be used: wash the biomass of fungal mycelium to get rid of culture medium, then put the biomass into sufficient amount of distilled water (1:100-1:200 by mass) for 5-6 hours at the temperature of 26° C. After steeping, collect the biomass and heat to boiling. Then, quickly cool on ice and centrifugate at 30000 g for 20 minutes.

Studies on bioluminescence of higher fungi have led to the conclusion that bioluminescence is based on a general two-stage process as follows: the first stage is formation of luciferin from a precursor catalyzed by a NAD(P)-H-dependent enzyme; the second stage is oxidation of luciferin under luciferase catalysis accompanied by t the emission of visible light (R. L. Airth, Characteristics of cell-free fungal bioluminescence, in Light and Life, ed. W. D. McElroy, B. Glass, Johns-Hopkins Press, Baltimore, 1961, pp. 262). However, until present, the chemical nature of the components of the bioluminescent system of higher fungi has not been established.

In 1966, Kuwabara and Wassink described luciferin emission from *Omphalia flavida*, but they did not provide any data on its chemical structure (S. Kuwabara and E. C. Wassink, in Bioluminescence in Progress, ed. F. H. Johnson and E. Y. Haneda, Princeton University Press, Princeton, 1966, p. 233). In 1970, Endo et al. isolated a fluorescent component from *Pleurotus japonicus* with fluorescence emission maximum at 530 nm (which is close to the emission maximum of fungal bioluminescence). This component was called illudin S. However, this substance did not show bioluminescent activity (M. Endo, M. Kajiwara and K. Nakanishi, Chem. Commun., 1970, 309). Later, in 1987-1988, Isobe et al. isolated riboflavin and lampteroflavin from the same source with the fluorescence emission maximum at 524 nm. However, these substances also did not show bioluminescent activity (M. Isobe, D. Uyakul and T. Goto, J. Biolumin. Chemilumin., 1987, 1, 181; M. Isobe, D. Uyakul and T. Goto, Tetrahedron Lett., 1988, 44, 1169). The candidates to the role of luciferin have also been isolated from *Mycena chlorophos* (S. Hayashi ey al. 2012. Biophysics Vol. 8, pp. 111-114) and *Panellus stipticus* (O. Shimomura et al. J Biolumin. Chemilumin. 1993, 8, 201-205; O. Shimomura et al Tetrahedron 1988, 44, 1597-1602, O. Shimomura Bioluminescence: Chemical Principles and Methods. CHAPTER 9 LUMINOUS FUNGI 2006, World Scientific, Singapore). However, no evidence has been provided in regard to their participation in bioluminescence. In 2009, Oliveira and Stevani described the isolated components of the bioluminescent systems of several fungi species: *Gerronema viridilucens, Mycena lucentipes* and *Mycena luxaeterna* (A. G. Oliveira and C. V. Stevani, Photochem. Photobiol. Sci., 2009, 8, 1416). They pointed out that the study on their structure was complicated due to a low concentration and low stability of these substances. The recent works of these researchers concerning a wide range of fungi have shown cross-reactions of "hot" and "cold" extracts of different species, thus proving a universal mechanism and similarity of the bioluminescent systems of all kinds of higher fungi (Oliveira et al. Photochemical &

Photobiological Sciences 2012, 11 (2): 848-52, Stevani et al. Photochemistry and Photobiology, 2013, 89: 1318-1326).

SUMMARY OF THE INVENTION

The Applicants have shown that hispidin is pre-luciferin (precursor) of fungal luciferin, 3-hydroxyhispidin is the fungal luciferin, and NAD(P)H-dependent hydroxylase (hereinafter referred to as hispidin-3-hydroxylase) is the enzyme which transforms pre-luciferin into luciferin. This discovery unveils manifold possibilities for analysing the activity of fungal luciferase in biological samples.

Also, the Applicants have shown that bisnoryangonin is also a precursor of luciferin, and 3-hydroxybisnoryangonin is another fungal luciferin.

Thus, the present invention provides methods and reagents for detecting luciferase in biological samples. The methods and reagents of the present invention allow for detection of fungal luciferase or functional analogs thereof. Similar systems based on coelenterazine have been designed to detect luciferase of coelenterates in biological samples; however, they cannot be applied to analyse luciferase of higher fungi and functional analogs thereof due to a different bioluminescence mechanism.

The present invention provides a method for detecting luciferase in the biological sample with the help of 3-hydroxyhispidin or a functional analog thereof comprising
  a) addition of 3-hydroxyhispidin to the sample;
  b) incubation of the reaction mixture under conditions which allow for a bioluminescent reaction;
  c) detection of bioluminescence of the reaction mixture.

In preferred embodiments, 3-hydroxyhispidin or a functional analog thereof (as for example, 3-hydroxybisnoryangonin) are added to the sample to a final concentration of 0.03 to 30 µM or, normally 1 to 5 µM. For example, 2.4 µM. In preferred embodiments, 3-hydroxyhispidin or a functional analog thereof (for example, 3-hydroxybisnoryangonin) are added to the sample in a buffer solution with a pH range of 6.0 to 9.8, normally 6.5 to 9.0, for example, 7.0 to 8.0. The mixture often contains reagents which increase the solubility of 3-hydroxyhispidin or of a functional analog thereof in water; as for example, detergents, such as Triton X-100 or nonylphenoxypolyethoxyethanol.

Also, the reaction mixture may contain components which stabilize and protect luciferase from inhibitive effect of trace amounts of heavy-metal ions, and from degradation caused by proteases. For example, the reaction mixture may contain dithiothreitol (DTT), beta-mercaptoethanol and/or EDTA. Also, the reaction mixture may contain protease inhibitors; for example, phenylacetic acid or oxalic acid.

The present invention also provides a method for detecting both luciferase and hispidin-3-hydroxylase with the help of hispidin or a functional analog thereof which includes:
  a) addition of hispidin or a functional analog thereof and NAD(P)H to the sample;
  b) incubation of the reaction mixture under conditions which allow for a bioluminescent reaction;
  c) detection of bioluminescence of the reaction mixture.

In preferred embodiments, hispidin or a functional analog thereof (for example, bisnoryangonin) are added to the sample to a final concentration of 0.03 to 30 µM, more often 1 to 5 µM; for example, 2.4 µM. In preferred embodiments, hispidin or its functional analog are added to the sample in a buffer solution with a pH range of 6.0 to 9.8, more often 6.5 to 9.0; for example, 7.2 to 8.0. The mixture often contains reagents which increase the solubility of hispidin or of a functional analog thereof in water; as for example, detergents, such as Triton X-100 or nonylphenoxypolyethoxyethanol.

NADPH or NADH are also added to the reaction mixture (at a final concentration of at least 20 µM; for example, 1-3 mM) preferably in a buffer solution with a pH range of 6.0 to 9.8 or, more often 6.5 to 9.0; for example, 7.2 to 8.0.

Also, the reaction mixture may contain components which stabilize and protect bioluminescent system enzymes from inhibitive effect of trace amounts of heavy-metal ions, and from degradation caused by proteases. For example, the reaction mixture may contain DTT, beta-mercaptoethanol and/or EDTA. Also, the reaction mixture may contain protease inhibitors; for example, phenylacetic acid or oxalic acid.

The present invention also provides reagents and kits for detecting luciferase in biological samples, which include 3-hydroxyhispidin (or a functional analog thereof) or hispidin (or a functional analog thereof) and NAD(P)H.

DETAILED DESCRIPTION

Figure 1:
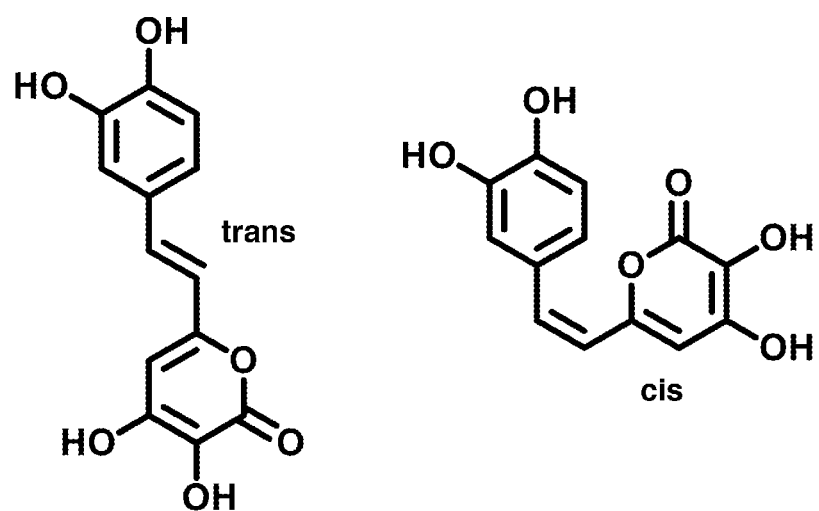
FIG. 1 shows the chemical structure of double bond stereoisomers of 3-hydroxyhispidin.

As mentioned above, the present invention provides methods for detecting luciferase activity in biological samples.

More particularly, the present invention provides a method for detecting luciferase in a biological sample with the help of 3-hydroxyhispidin or a functional analog thereof. The method includes:
a) addition of hispidin or a functional analog thereof and NAD(P)H to the sample;
b) incubation of the obtained reaction mixture under conditions which allow for bioluminescent reaction;
c) detection of bioluminescence of the reaction mixture.

The present invention further provides a method for detecting luciferase and hispidin-3-hydroxylase in a biological sample with the help of hispidin or a functional analog thereof. The method includes:
a) addition of hispidin or a functional analog thereof and NAD(P)H to the sample;
b) incubation of the obtained reaction mixture under conditions which allow for bioluminescent reaction;
c) detecting bioluminescence of the reaction mixture.

The reagents and kits for implementing the methods of this invention are also provided.

Before the subject invention is described further, it is to be understood that the invention is not limited to the particular embodiments of the invention described below, as variations of the particular embodiments may be made and still fall within the scope of the invention.

Biological Samples

Implementation of methods of the present invention provides the appearance of luminescence of a reaction mixture containing a biological sample, when the sample contains luciferase which employs 3-hydroxyhispidin or a functional analog thereof (as for example, 3-hydroxybisnoryangonin) as substrate (i.e. luciferin). For example, such luciferase can be found in higher fungi which are capable of bioluminescence.

The investigated sample may also contain hispidin-3-hydroxylase which is capable of transforming hispidin or a functional analog thereof into substrate for luciferase. For example, higher fungi capable of bioluminescence contain hispidin-3-hydroxylase.

Biological samples may be obtained using various techniques known in biology and comprise samples of tissues, cells, extracts, homogenates, protein mixtures of various degrees of purification, etc. As for example, biological samples can be obtained from higher fungi.

Biological samples may also contain isolated components (luciferase or luciferase and hispidin-3-hydroxylase) of bioluminescent systems of higher fungi or their functional analogs.

As used herein the term "isolated" is meant to describe a component that is an environment different from that in which the component naturally occurs. For example, the corresponding component is obtained in substantial purity. The "substantial purity" means that the protein is at least about 20% pure, often at least 30% pure, normally 50% pure, or at least 90% pure.

In order to isolate proteins, any normal techniques for protein purification may be used; for example, the ones which are described in Guide to Protein Purification, (Deuthser ed.) (Academic Press, 1990). For example, the original source may be used for lysate or cold extract preparation, which are then purified using HPLC, size exclusion chromatography, gel electrophoresis, affinity chromatography, etc. Protein preparations may be tested for the presence of active luciferase or a complex of luciferase and hispidin-3-hydroxylase using the methods of the present invention.

Biological samples may also express recombinant luciferase or luciferase and hispidin-3-hydroxylase or their functional mutants. Nucleic acid sequences used for expression of the said proteins may be obtained from natural sources (as for example, from higher fungi) or synthesized. Currently, a number of methods are established that allow to clone genes encoding proteins with known activity. Such methods have been partially described in Maniatis, T., et al. (Molecular Cloning—A Laboratory Manual Cold Spring Harbor Laboratory, Cold Spring Harbor, N.Y. 1982) and Newman and Campagnoni (Neuromethods, v. 16, 1990, pp 13-48). For example, an expression library in appropriate host cells may be prepared and tested for luciferase activity. Or, protein may be isolated from cold extract to determine its partial amino acid sequence, and then, an appropriate cDNA from cDNA sample from a higher fungus may be cloned. Nucleic acid sequences must be inserted into an expression cassette. The expression cassette may exist as an extrachromosomal element or may be integrated into the genome of the cell as a result of introduction of said expression cassette into the cell. In the expression cassette, subject nucleic acids operably linked to a regulatory sequence that can include promoters, enhancers, terminators, operators, repressors and inducers. After introducing the expression cassette into a cell, a functional protein may be formed therein. For expression, any convenient expression system may be used, including, for example, bacterial, yeast, insect, amphibian, or mammalian systems. Methods for preparing expression cassettes or systems capable of expressing the desired product are known for a person skilled in the art. Cell lines that stably express luciferase or luciferase and hispidin-3-hydroxylase can be selected by the methods known in the art known in the art (e.g. co-transfection with a selectable marker such as dhfr, gpt, neomycin, hygromycin allows the identification and isolation of the transfected cells that contain the gene integrated into a genome). The above-described expression systems can be used in prokaryotic or eukaryotic hosts. Host-cells such as *E. coli, B. subtilis, S. cerevisiae*, insect cells in combination with baculovirus vectors, or cells of a higher organism such as vertebrates, e.g., COS 7 cells, HEK 293, CHO, *Xenopus oocytes*, etc., may be used for production of the protein.

Also, functional mutants of natural proteins can be expressed. As used in the present description, the term "functional" in regard to luciferase means that the said protein is capable of using 3-hydroxyhispidin or its double bond cis-isomer as luciferin. As used in the present description, the term "functional" in regard to hispidin-3-hydroxylase means that the mutant protein is capable of transforming hispidin or bisnoryangonin into 3-hydroxyhispidin or 3-hydroxybisnoryangonin, correspondingly, in the presence of NAD(P)H and atmospheric oxygen.

As used in the present description, the term "mutant" refers to the protein which is obtained by adding and/or deleting and/or replacing at least one amino acid residue within the native protein or at the N- and/or C-terminus of a protein. As used in the present description, the term "mutant" refers to the nucleic acid molecule which encodes the mutant protein. Besides, the term "mutant" refers to any shorter or longer variant of an appropriate protein or a nucleic acid.

The modifications, additions or deletions can be introduced by any method known in the art (see for example Gustin et al., Biotechniques (1993) 14: 22; Barany, Gene (1985) 37: 111-123; and Colicelli et al., Mol. Gen. Genet. (1985) 199:537-539, Sambrook et al., Molecular Cloning: A Laboratory Manual, (1989), CSH Press, pp. 15.3-15.108) including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-directed mutagenesis, random mutagenesis, gene reassembly, gene site saturated mutagenesis (GSSM), synthetic ligation reassembly (SLR), or a combination thereof. The modifications, additions or deletions may be also introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

A reference to a nucleotide sequence which "encodes" polypeptide means that such polypeptide is produced from a nucleotide sequence during mRNA translation and transcription. For this, both a coding strand, which is identical to mRNA and commonly used in the sequence listing, and a complementary strand, which is used as a template during transcription, can be specified. It will be appreciated by those having skill in the art that the term also includes any degenerated nucleotide sequences that encode the same polypeptides. "Nucleotide sequences encoding polypeptide" include sequences which contain introns.

Reagents for Detecting Luciferase Activity

The methods of the present invention are based on the use of 3-hydroxyhispidin and a functional analog thereof for detecting luciferase activity in biological samples.

As used in the present description, the term "3-hydroxyhispidin" refers to (E)-6-(3,4-dihydroxystyryl)-3,4-dihydroxy-2H-pyran-2-one. Since the substance tends to isomerize in a solution and forms equilibrium mixtures of double bond cis- and trans-isomers, the term "3-hydroxyhispidin", for the purposes of the present invention, also relates to the double bond cis-isomer thereof (Z)-6-(3,4-dihydroxystyryl)-3,4-dihydroxy-2H-pyran-2-one. The chemical structures of the trans-isomer of 3-hydroxyhispidin and its double bond cis-isomer are shown in FIG. 1.

3-hydroxyhispidin shows stability during chromatography in a water-acetonitrile mixture with addition of formic acid (the final concentration is 0.1%) during one day. Lyophilized substrate is kept at −20° C. with no activity loss for no less than 30 days, often no less than 60 days, normally no less than a year.

3-hydroxyhispidin is readily soluble in aprotic solvents (DMSO, acetonitrile, acetone, etc.) and moderately soluble in water.

3-hydroxyhispidin is stable within a wide range of temperatures; for example, it can sustain short-term boiling in a water solution.

3-hydroxybisnoryangonin, which is a functional analog of 3-hydroxyhispidin, may also be used.

As used in the present description, the term "3-hydroxybisnoryangonin" refers to (E)-3,4-dihydroxy-6-(4-hydroxystyryl)-3,4-dihydroxy-2H-pyran-2-one. Since the substance tends to isomerize in a solution and forms equilibrium mixtures of double bond cis- and trans-isomers, the term "3-hydroxybisnoryangonin", for the purposes of the present invention, also relates to the double bond cis-isomer thereof (Z)-3,4-dihydroxy-6-(4-hydroxystyryl)-2H-pyran-2-one.

Figure 2:
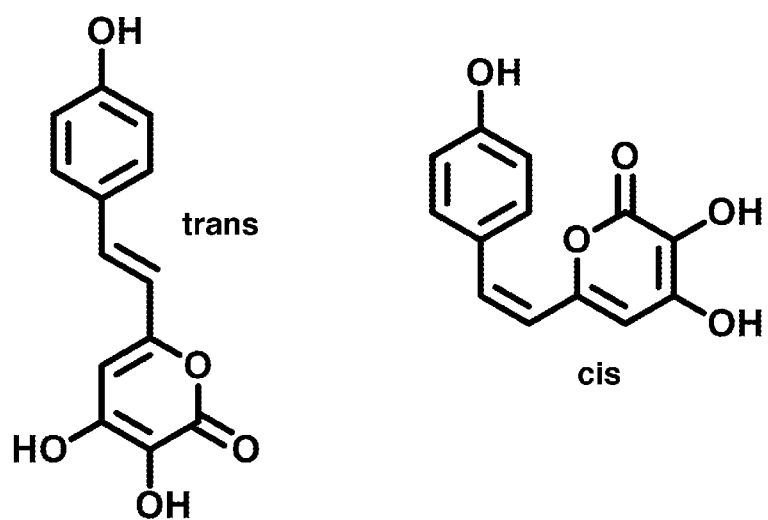
FIG. 2 shows the chemical structure of double bond stereoisomers of 3-hydroxybisnoryangonin.

The chemical structures of 3-hydroxybisnoryangonin trans-isomer and a double bond cis-isomer thereof are shown in FIG. 2.

3-hydroxyhispidin and 3-hydroxybisnoryangonin can be obtained by enzymatic synthesis from hispidin or bisnoryangonin, correspondingly, in the presence of hispidin-3-hydroxylase, NADPH (or NADH) and atmospheric oxygen.

The following conditions are preferred for the synthesis: the pH is within the range of 6.5 to 9.0, the NAD(P)H concentration is 1-20 mM; as for example, 10 mM. The reaction mixture may contain components which stabilize and protect hispidin-3-hydroxylase from inhibitive effect of trace amounts of heavy-metal ions, and from degradation caused by proteases. For example, the reaction mixture may contain DTT, beta-mercaptoethanol and/or EDTA. The reaction mixture may further contain protease inhibitors. The reaction mixture may further contain detergents, such as Triton X-100 or nonylphenoxypolyethoxyethanol. The reaction mixture may further contain admixtures of DMSO, acetonitrile and other solvents. An example of conditions for enzymatic synthesis is shown in the experimental section below.

The obtained substances may be isolated from the reaction mixture by extraction using the following solvents: water, alcohol, acetonitrile, DMSO or the mixtures thereof, or non-water-miscible solvents: ethyl acetate, chloroform, dichloromethane and others, with subsequent liquid chromatography separation of the obtained extract or without such separation. The detailed description of one of the possible schemes to isolate 3-hydroxyhispidin is given in the experimental section below.

Alternatively, 3-hydroxyhispidin and 3-hydroxybisnoryangonin can be obtained by chemical synthesis.

3-hydroxyhispidin or a functional analog thereof are soluble in water, a buffer solution, DMSO, alcohol, acetonitrile or a mixture thereof. The obtained solution can be diluted to a working concentration by water, buffer solution and 0.01-1% formic acid solution. The appropriate buffer solutions include a phosphate buffer, Tris HCl, HEPES and others, commonly used within the pH range of 6.0 to 9.8, normally 6.5 to 9.0, as a rule 7.0 to 8.0. In preferred embodiments, the reagents which increase water solubility of 3-hydroxyhispidin and a functional analog thereof are added to the mixture. They include, for example, detergents, such as Triton X-100 or nonylphenoxypolyethoxyethanol.

The term "working concentration" is used herein to define the concentrations of the solution which is added to the biological sample.

In case the biological sample contains luciferase and hispidin-3-hydroxylase, the luciferin precursor (e.g. hispidin or a functional analog thereof) together with NAD(P)H are used to detect them.

Figure 6:
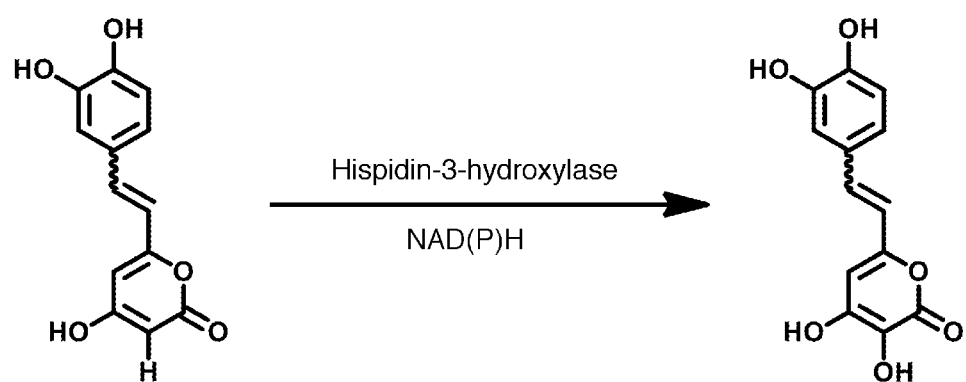
FIG. 6 illustrates the hydroxylation process of hispidin and functional analogs thereof at position 3 of the pyrone ring under the influence of hispidin-3-hydroxylase in the presence of NAD(P)H.

In the presence of NAD(P)H, hispidin-3-hydroxylase hydroxylases hispidin and functional analogs thereof at position 3 of the pyrone ring, as shown in FIG. 6. 3-hydroxyhispidin and functional analogs thereof serve as substrates for luciferase.

Figure 3:
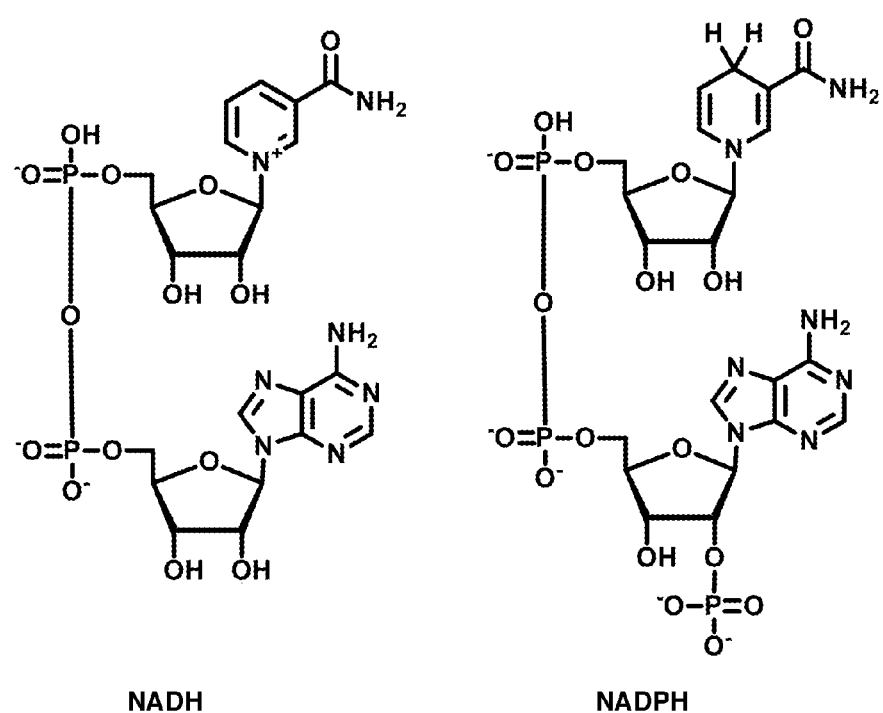
FIG. 3 shows the chemical structure of reduced forms of nicotinamide adenine dinucleotide phosphate (NADPH) and nicotinamide adenine dinucleotide (NADH).

As used in the present description, the term "NAD(P)H" means the reduced form of nicotinamide adenine dinucleotide phosphate (NADPH) or the reduced form of nicotinamide adenine dinucleotide (NADH). The structures of nicotinamide adenine dinucleotide phosphate and nicotinamide adenine dinucleotide are shown in FIG. 3.

Figure 4:
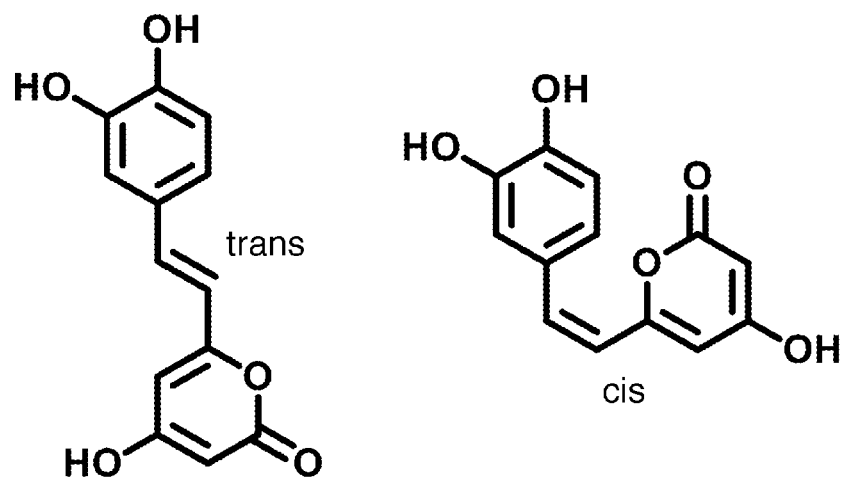
FIG. 4 shows the chemical structure of double bond stereoisomers of hispidin.

Hispidin (or (E)-6-(3,4-dihydroxystyryl)-4-hydroxy-2H-pyran-2-one) is a well-known compound which relates to the group of styrylpyrones isolated from a number of fungi and plants (Beckert et al. Phytochemistry, VoL 44, No. 2, pp. 275-283, 1997; In-Kyoung Lee and Bong-Sik Yun The Journal of Antibiotics (2011) 64, 349-359). Since the substance tends to isomerize in solution and forms equilibrium mixtures of double bond cis- and trans-isomers, the term "hispidin", for the purposes of the present invention, also relates to the double bond cis-isomer thereof (Z)-6-(3,4-dihydroxystyryl)-4-hydroxy-2H-pyran-2-one. The chemical structures of the double bond trans- and cis-isomers of hispidin are shown in FIG. 4.

Bisnoryangonin, which is a functional analog of hispidin, may also be used.

Figure 5:
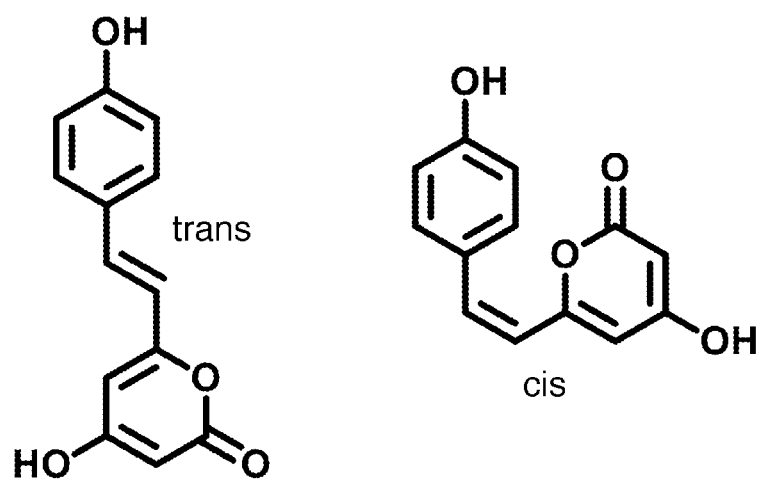
FIG. 5 shows the chemical structure of double bond stereoisomers of bisnoryangonin.

As used herein, the term "bisnoryangonin" refers to (E)-4-hydroxy-6-(4-hydroxystyryl)-2H-pyran-2-one. Since the substance tends to isomerize in a solution and forms equilibrium mixtures of double bond cis- and trans-isomers, the term "bisnoryangonin", for the purposes of the present invention, also relates to the double bond cis-isomer thereof (Z)-4-hydroxy-6-(4-hydroxystyryl)-2H-pyran-2-one. The chemical structures of the double bond trans- and cis-isomers of bisnoryangonin are shown in FIG. 5.

Hispidin or a functional analog thereof can be dissolved in water, buffer solution, DMSO, alcohol, acetonitrile or the mixture thereof. The obtained solution can be diluted to a working concentration using water, buffer solution or 0.01-1% formic acid solution. The appropriate buffer solutions include a phosphate buffer, Tris HCl, HEPES and others, commonly used within the pH range of 6.0 to 9.8, normally 6.5 to 9.0, as a rule 7.0 to 8.0. In preferred embodiments, the reagents which increase water solubility of 3-hydroxyhispidin and a functional analog thereof are added to the mixture; for example, detergents, such as Triton X-100 or nonylphenoxypolyethoxyethanol. In preferred embodiments, the reagents which increase water solubility of hispidin and a functional analog thereof are added to the mixture; for example, detergents, such as Triton X-100 or nonylphenoxypolyethoxyethanol.

Conditions for Developing Bioluminescent Signal

Formation of bioluminescence depends on the amount and integrity of luciferase or luciferase and hispidin-3-hydroxylase in biological samples.

Signal formation is effected by the pH of the reaction mixture. Bioluminescent signal formation occurs within the pH range of 6.0 to 9.8, normally 6.5 to 9.0, preferably 7.0 to 8.0. To maintain the pH, any standard buffer solutions for the given pH range can be used, including a phosphate buffer, HEPES, Tris HCl. In preferred embodiments, the molar concentration of a buffer solution does not exceed 2, as for example, the molar concentration does not exceed 1, more often it is within the range of 0.05 to 0.4, normally 0.1 to 0.2.

Also, for the purposes of the present invention, the reaction mixtures may contain components which stabilize and protect bioluminescent system enzymes from inhibitive effect of trace amounts of heavy-metal ions, and from degradation caused by proteases.

For example, the reaction mixture may contain DTT at a concentration of no more than 20 mM, more often at a concentration of 0.1 to 8 mM, preferably at a concentration of 0.1 to 4 mM.

The reaction mixture may also contain beta-mercaptoethanol and/or EDTA at a final concentration of 0 to 5 mM.

For example, the reaction mixture may contain 0.1 to 2 mM DTT and 0.1 to 1 mM EDTA.

The reaction mixture may further contain protease inhibitors; for example, phenylacetic acid or oxalic acid at standard concentrations.

For the purposes of the present invention, 3-hydroxyhispidin or a functional analog thereof is added to the biological sample to a final concentration of 0.03 to 30 µM, more often 1 to 5 µM.

In some embodiments, a reagent mixture comprising a buffer solution, components which stabilize and protect bioluminescent system enzymes from inhibitive effect of trace amounts of heavy-metal ions, and from degradation caused by proteases, and 3-hydroxyhispidin is added. In other embodiments, a buffer solution, components which stabilize and protect bioluminescent system enzymes from inhibitive effect of trace amounts of heavy-metal ions, and from degradation caused by proteases are added to the sample in the first place, and then, a 3-hydroxyhispidin solution is added.

For the purposes of the present invention, hispidin or a functional analog thereof is added to the biological sample at a final concentration of 0.03-30 µM, more often 1 to 5 µM, for example, 2.4 µM.

NAD(P)H is added to the biological sample together with hispidin, or before or after the addition hispidin or a functional analog thereof at a final concentration 0.01 to 10 mM, more often 0.4-2 mM, normally 1 mM.

In some embodiments, a reagent mixture is added to the sample, which includes a buffer solution, components which stabilize and protect bioluminescent system enzymes from inhibitive effect of trace amounts of heavy-metal ions, and from degradation caused by proteases, NAD(P)H and hispidin or a functional analog thereof.

For example, 100 µl mixture containing 0.1 M phosphate buffer, pH 7.5, 0.1 mM DTT, 2.4 µM hispidin, 0.01% Triton X-100, 0.4 mM NAD(P)H is added to the sample (1-5 µl).

In some embodiments, two reagent mixtures are sequentially added to the sample, one of which contains NAD(P)H, and the other contains hispidin or a functional analog thereof.

For example, 100 µl mixture containing 0.1 M phosphate buffer, pH 7.5, 0.1 mM DTT, 2.4 µM µg hispidin (or a functional analog thereof), 0.01% Triton X-100 is added to the sample in the first place, and then, 4 µl 10 mM NAD(P)H water solution is added to the sample (1-5 µl) to initiate the reaction.

In some embodiments, 100 µl mixture containing 0.1 M phosphate buffer, pH 7.5, 0.1 mM DTT, 0.4 mM µg NAD(P)H is added to the sample (1-5 µl) in the first place, and then 4 µl 64 µM aqueous solution of hispidin or a functional analog thereof in an aqueous solution containing 0.01% Triton X-100 and 0.1% formic acid.

Depending on the solvent used for preparing the solution of hispidin, 3-hydroxyhispidin or functional analogs thereof, the reaction mixture may contain small amounts of solvents used.

The reaction mixture may also contain detergents, such as Triton X-100 or nonylphenoxypolyethoxyethanol. In preferred embodiments, the concentration of detergents in the reaction mixture does not exceed 0.2%, more often 0.1%, optimally 0.06%.

The examples of measuring luciferase activity in the biological samples additionally containing hispidin-3-hydroxylase are given in the experimental section below.

Also, the reaction mixture may contain bovine serum albumin (BSA) or other proteins at concentrations not exceeding 2%, more often not exceeding 1%, optimally not exceeding 0.5%. BSA is used if the concentration of the biological sample is extremely low; in such a case, BSA serves as a protein stabiliser.

The bioluminescent signal develops in a wide range of temperatures, from 0 to 40° C., optimally at 20-25° C.

Formation of the luminescent signal starts immediately after reaction initiation, when the above mentioned key reagents are added for detecting luciferase activity. Intensity of luminescence increases over time after reaction initiation, as a rule, within 5 to 30 minutes, for example, within 10 minutes. Then, exponential decay takes place, the speed of which is determined by enzyme activity and original substrate concentrations. Under certain conditions, when the concentrations of the substrates are high, enzyme activities are low, and the reaction temperature is lowered, the reaction may be observed for 24 hours or more.

Bioluminescence Detection

The methods of the present invention include the detection of bioluminescence which is produced in the luciferase-containing biological sample after the appearance of luciferin therein.

Bioluminescence may be detected by the methods known by those skilled in the art, more particularly, using visual screening or a luminometer, photometer, fluorimeter, digital camera or sensitive film. The quantitative characteristic may be determined as the maximum luminescence intensity, which is attained in 5 to 30 minutes after bioluminescent reaction initiation, or by luminescence growth rate within the interval of up to 30 minutes after bioluminescent reaction initiation; for example, within the interval of 5, 10, 20, 30, 60 or more seconds after reaction initiation.

In preferred embodiments, the measured luminescence is represented by long-lasting light emission rather than light flashes. In preferred embodiments, luminescence intensity depends on the activity of the bioluminescent system enzymes present in the sample, initial substrate concentrations and reaction mixture temperature and normally ranges from 10 kV/s to 10 million kV/s, more often 100 to 100 000 kV/s.

Luminescence intensity depends on the reagents used. For example, in accordance with the method of the present invention, the maximum intensity of sample luminescence is approximately 10 times lower in case of the addition of bisnoryangonin as compared to using hispidin. Also, the maximum intensity of sample luminescence is two or three times lower when NADH is added as compared to adding NADPH.

The reaction lasts no less than 30 minutes after initiation, more often 30 to 60 minutes, sometimes (depending on the conditions) hours or even days.

Methods of Use

The methods and reagents of the present invention find use in a wide spectrum of in vivo and in vitro bioluminescent assays.

More particularly, the methods and reagents of the present invention may be used for detecting active components of the bioluminescent system of higher fungi in the process of purification thereof.

Also, methods and reagents of the present invention may be used for detecting functional analogs of the enzymes of the fungal bioluminescent system in biological samples.

Also, the methods and reagents of the present invention may be used for detecting activity of recombinant luciferase or luciferase and hispidin-3-hydroxylase in host cells.

In some embodiments, luciferase-coding nucleic acid should be obtained for the application. The obtained nucleic acid should be inserted into an expression cassette which provides short-term and long-term expression of this nucleic acid in host cells. The expression cassette may contain elements which provide address delivery of the construct to the cells or cell compartments of interest, or be a part of the particles which provide address delivery. After transfection of cells with an expression cassette (as for example, as part of an expression vector) and after the time required for expression product to develop in cells, the luciferase activity within the cells and in cell lysate may be detected.

In some embodiments, nucleic acids which encode luciferase and hispidin-3-hydroxylase should be obtained for the application. The obtained nucleic acid should be inserted into the expression cassettes which provide short-term and long-term expression of this nucleic acid in host cells; for example, under the promoters of interest. The expression cassettes may contain elements which provide address delivery of the construct to the cells or cell compartments of interest, or be a part of the particles which provide address delivery. After transfection of cells with an expression cassette (as for example, as part of an expression vector) and after the time required for expression product to develop in cells, simultaneous presence of luciferase and hispidin-3-hydroxylase within the cells and in cell lysate may be detected.

Kits

Also provided by the present invention are kits for use in practicing one or more of the above-described applications.

In some embodiments, kits typically include 3-hydroxyhispidin and/or a functional analog thereof, preferably with a buffer solution for dissolving the said substrate and/or addition thereof to the biological samples. 3-hydroxyhispidin and/or a functional analog thereof may exist in a dissolved state in an appropriate storage medium, such as a DMSO, water or buffer solution with a detergent, normally in an appropriate container. Alternatively, 3-hydroxyhispidin and/or a functional analog thereof may be included in a kit in a lyophilized state.

In other embodiments, kits typically include hispidin and/or a functional analog thereof, preferably with a buffer solution for dissolving the said substrate and/or addition thereof to the biological samples. In preferred embodiments, kits also comprise NAD(P)H, preferably with a buffer solution for dissolving the said substrate and/or addition thereof to the biological samples.

In addition to the above components, the subject kits will further include instructions for practicing the subject methods. These instructions may be present in the subject kits in a variety of forms, one or more of which may be present in the kit (e.g. a hard copy or a digital copy in the form of a text and/or image file).

The following example is offered by way of illustration and not by way of limitation.

EXAMPLES

Example 1

Detecting Luciferin Precursor in Fruiting Bodies of Higher Fungi

The mycelium of a number of bioluminescent fungi was used for preparing hot extracts: *Neonothopanus nambi* was collected in the forests of southern Vietnam, *Mycena citricolor* was collected from ATCC #12578, *Panellus stipticus* was collected in Ottawa (Canada), Armillaria borealis was collected near Krasnoyarsk (Russia). The mycelium of Neonothopanus nambi was grown in a medium which contains potato broth at a concentration of 200 g/L and sucrose at a concentration of 20 g/l for 5 days at 24° C. with constant mixing at 160-180 rpm. The mycelium of other fungi was grown in a medium which contains potato broth at a concentration of 200 g/l and glucose at a concentration of 20 g/L, under similar conditions: A. borealis for 12 days at 24° C., P. stipticus for 5-7 days at 24° C. and M. citricolor for 5-7 days at 27° C.

Also, fruiting bodies of a number of non-bioluminescent fungi collected in a forest nearby Krasnoyarsk were used for preparing hot extracts: Pholiota squarrosa, Tricholoma sp., Phellinus sp., Russula foetens and Clitocybe sp. In each case, to prepare the hot extracts, 10 g of a fruiting body or mycelium was put in 30 ml of distilled water, then, it was homogenized and heated till boiling in a microwave oven. Thereafter, the extracts were quickly cooled on ice and centrifuged at 20000 g for 20 minutes at 4° C. The supernatant was separated using 40 mL of ethyl acetate, then, it was concentrated on a rotary evaporator and diluted with 200 µl of 30% DMSO containing 0.1% formic acid.

The obtained extracts were tested in a bioluminescent test described by Oliveira and Stevani (Photochem. Photobiol. Sci., 2009, 8, 1416) using a cold extract from Neonothopanus nambi.

In order to obtain a cold extract, the mycelium was washed to get rid of culture medium, then, it was put into a 200-fold amount of distilled water for 15 hours at 26° C. Thereafter, the mycelium was separated from water by centrifugation, then, it was homogenized on ice in 10 volumes of 0.2 M phosphate buffer, pH 7.5 and sonicated on ice for 10 minutes using Ultrasonic disintegrator UD-20. The homogenate was centrifuged at 30000 g at 4° C. for 20 minutes. The obtained cold extract was stored at −20° C.

Figure 7:
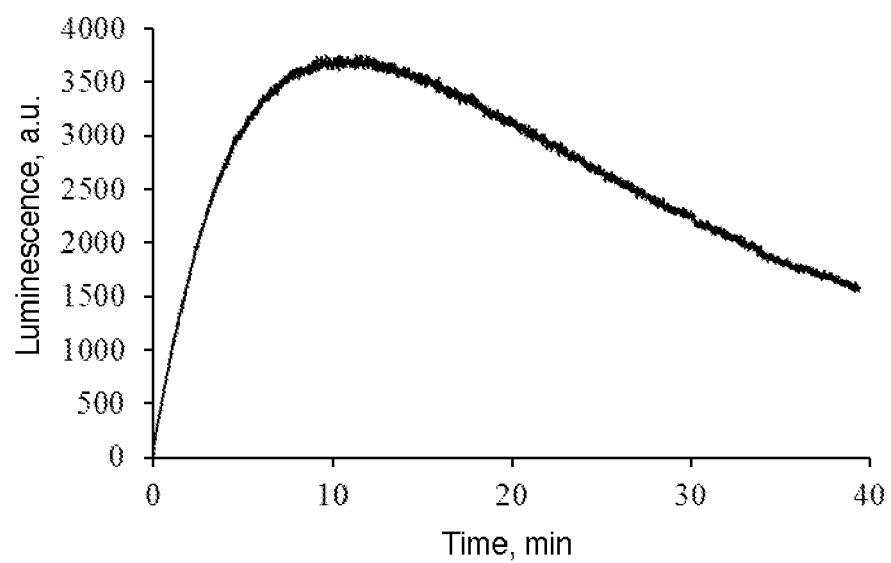
FIG. 7 illustrates the result of bioluminescence measuring.

500 µl of the following components were mixed for a bioluminescent test: 25 µL of cold extract, 2 µL of hot extract, 442 µL 0.2 M phosphate buffer, pH 7.5, 1 µL 1 M DTT and 10 µL 1% Triton X-100. The bioluminescent reaction was initiated in a Glomax 20/20 (Promega, USA) luminometer cuvette by adding 20 µL 20 mM NADPH. Luminescence was measured at 23±1° C. The typical results of measurements are shown in FIG. 7. The luciferin precursor was detected in the fruiting bodies of all non-bioluminescent fungi at a concentration significantly greater than that in the mycelium of bioluminescent fungi.

Example 2

Determining Structure of Luciferin Precursor of Higher Fungi

Figure 8:
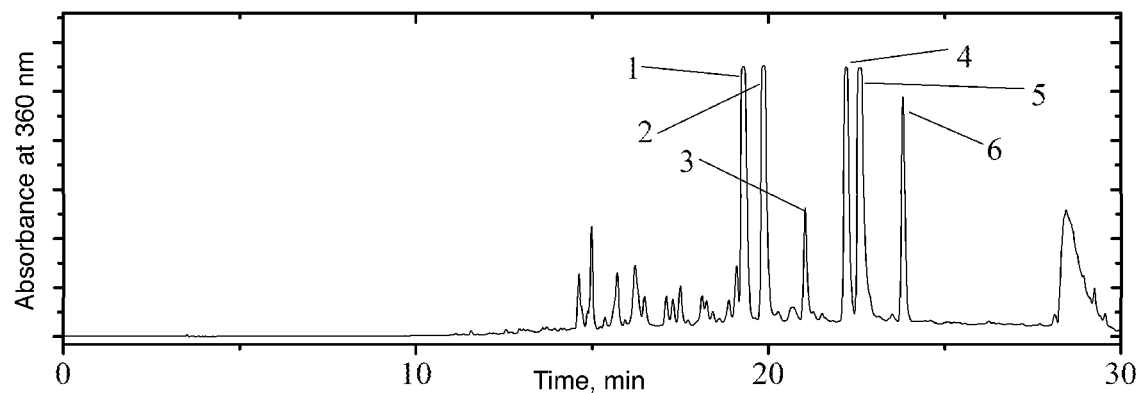
FIG. 8 illustrates the result of reversed-phase HPLC of the hot extract from the fruiting bodies of *Ph. squarrosa*.

The hot extract of the fruiting bodies of Ph. squarrosa obtained as described in Example 1 was used for reversed-phase HPLC which allowed identifying six different fractions: 1-6 (FIG. 8).

All the 6 fractions showed activity in the bioluminescent test in the presence of the cold extract from Neonothopanus nambi, as described in Example 1. The maximum luminescence of fractions 1-6 was 24000, 80, 6670, 40, 1300 and 1000 correspondingly (a signal-to-noise ratio of the luminometer, the values were normalised against optical density at 360 nm).

Besides, rechromatography of the obtained fractions showed that fraction pairs (1, 3) and (5, 6) were hispidin and bisnoryangonin forming equilibrium mixtures of double bond cis- and trans-isomers of these substances (FIG. 4, 5).

All the six fractions underwent rechromatography and were used for obtaining NMR spectra: $^1$H, 2D DQF-COSY, 2D $^1$H-$^{13}$C HSQC and 2D $^1$H-$^{13}$C HMBC. These data, in combination with HRMS (high-resolution mass spectra) made it possible to determine the chemical structures of the substances. The spectra of compounds (1, 3) and (5, 6) were totally identical and contained two sets of signals corresponding to hispidin and its double bond cis-isomer (1, 3) and bisnoryangonin and its double bond cis-isomer (5, 6). Compound 2 was identified as a hispidin homodimer (3.3-bishispidinyl) and compound 4 was identified as a heterodimer of hispidin and bisnoryangonin (3-bisnoryangonyl-14-hispidin).

The structural identity of compounds 1, 3, 5, 6 with the said substances was confirmed by comparing their chromatograms and spectra with the chromatograms and spectra of commercially available hispidin (Sigma, USA) and synthetic bisnoryangonin. Thus, the coincidence of the chromatographic retention times of compounds 1, 3 and the retention times or commercially available hispidin and its isomer was observed, and the correspondence of the chromatographic retention times of compounds 5, 6 with the retention times or synthetic bisnoryangonin and its cis-isomer was observed. Also, the coincidence of the chemical shifts in $^1$H and $^{13}$C in NMR spectra for substances 1, 3 with those of commercially available hispidin and its cis-isomer was observed, and the coincidence of chemical shifts in $^1$H and $^{13}$C in NMR spectra for substances 5, 6 with those of commercially available synthetic bisnoryangonin and its cis-isomer was detected. The tables of chemical shifts of substances 1, 3, 5, 6 are given in Table 1.

TABLE 1

Chemical shifts of compounds 1, 3 in DMSO-$d_6$ and 5, 6 in acetone-$d_6$. Atom numbering is as per FIG. 4 and 5.

| | trans-hispidin (1) | | cis-hispidin (3) | | trans-bisnoryangonin (5) | | cis-bisnoryangonin (6) | |
|---|---|---|---|---|---|---|---|---|
| Atom | δH | δC | δH | δC | δH | δC | δH | δC |
| 2 | | 162.82 | | 162.82 | | 162.85 | | 162.85 |
| 3 | 5.23 (s) | 89.50 | 5.22 (s) | 88.69 | 5.38 (d, 1.9 Hz) | 89.83 | 5.37 (d, 1.9 Hz) | 90.2 |
| 4 | | 169.85 | | 169.56 | | 169.92 | | 169.50 |
| 5 | 6.13 (s) | 101.3 | 6.07 (s) | 102.64 | 6.14 (d, 1.9 Hz) | 100.11 | 6.11 (d, 1.9 Hz) | 101.52 |
| 6 | | 160.35 | | 160.35 | | 160.32 | | 160.32 |
| 7 | 6.67 (d, 16 Hz) | 116.91 | 5.98 (d, 12 Hz) | 118.33 | 6.75 (d, 16 Hz) | 116.67 | 6.045 (d, 12 Hz) | 118.38 |

TABLE 1-continued

Chemical shifts of compounds 1, 3 in DMSO-$d_6$ and 5, 6 in acetone-$d_6$. Atom numbering is as per FIG. 4 and 5.

| Atom | trans-hispidin (1) δH | δC | cis-hispidin (3) δH | δC | trans-bisnoryangonin (5) δH | δC | cis-bisnoryangonin (6) δH | δC |
|---|---|---|---|---|---|---|---|---|
| 8 | 7.12 (d, 16 Hz) | 134.81 | 6.63 (d, 12 Hz) | 137.13 | 7.35 (d, 16 Hz) | 134.64 | 6.76 (d, 12 Hz) | 136.67 |
| 9 |  | 127.26 |  | 127.07 |  | 127.28 |  | 127.09 |
| 10 | 7.03 (d, 2.0 Hz) | 114.47 | 6.87 (d, 2.0 Hz) | 116.93 | 7.55 (d, 8.6 Hz) | 129.22 | 7.43 (d, 8.6 Hz) | 131.25 |
| 11 |  | 145.95 |  | 145.20 | 6.91 (d, 8.6 Hz) | 115.83 | 6.84 (d, 8.6 Hz) | 115.04 |
| 12 |  | 147.88 |  | 146.63 |  | 158.95 |  | 158.14 |
| 13 | 6.77 (d, 8.1 Hz) | 116.16 | 6.70 (d, 8.1 Hz) | 115.64 | 6.91 (d, 8.6 Hz) | 115.83 | 6.84 (d, 8.6 Hz) | 115.04 |
| 14 | 6.95 (dd, 8.1; 2.0 Hz) | 120.73 | 6.78 (dd, 8.1; 2.0 Hz) | 121.82 | 7.55 (d, 8.6 Hz) | 129.22 | 7.43 (d, 8.6 Hz) | 131.25 |

Figure 9:
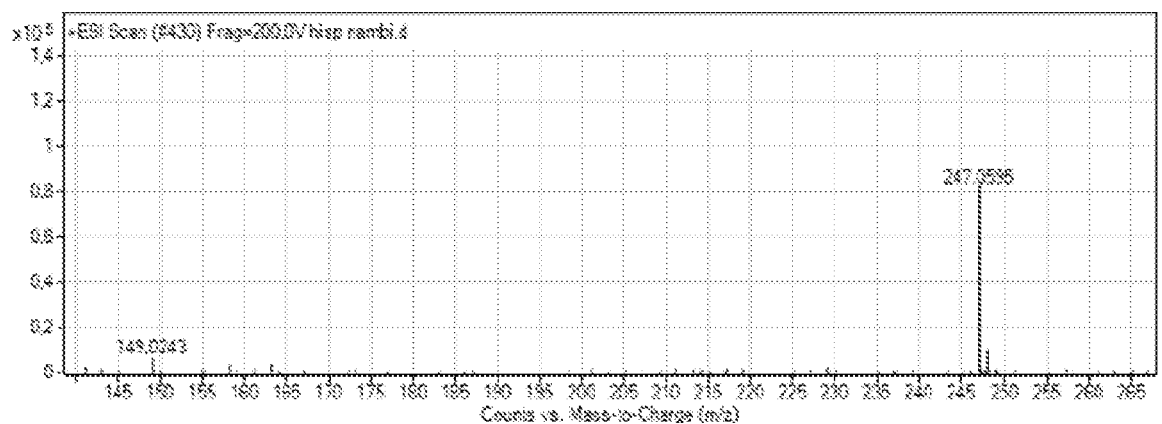
FIG. 9 shows HRMS spectrum of hispidin isolated from *N. nambi*.

In order to confirm the role of hispidin as a luciferin precursor in luminous fungi, hispidin was isolated from the luminous mycelium of *N. nambi*. The preliminary experiments showed that soaking of the mycelium in distilled water for one night results in a sudden increase in activity of hot and cold extracts (up to 250 and 140 times, correspondingly). The preparation of a hot extract obtained from this soaked mycelium of *N. nambi* followed by HPLC resulted in isolation of two compounds with retention times and UV-spectra identical to those of trans-hispidin and a double bond cis-isomer thereof. Besides, these two compounds showed tautomerization, specific bioluminescent activity and HRMS (FIG. 9) identical to those of trans-hispidin and a cis-isomer thereof obtained from the fruiting bodies of *Ph. squarrosa*.

Overall, 0.5 µg of the tautomer mixture of hispidin and a cis-isomer thereof were separated from 10 g of mycelium.

The presence of hispidin and a cis-isomer thereof was further confirmed by chromatography of the hot extracts of different bioluminescent fungi obtained as shown in Example 1.

Example 3

Synthesis, Purification and Identification of Luciferin of Higher Fungi

A ~35 kDa fraction containing partially purified preparation of NADPH-dependent enzyme of the fungal bioluminescent system was obtained from the cold extract of *N. nambi* obtained as described in Example 2 by chromatography using Superdex 75 (Sigma-Aldrich, USA). Also, a luminescence-capable microsomal fraction (a fraction of protein components with molecular weights over 200 kDa) of the cold extract was obtained. Synthetic hispidin (Sigma-Aldrich, USA) was incubated with a ~35 kDa fraction in the presence of NADPH. The reaction mixture comprised 5 mL 0.2 M phosphate buffer (pH 7.5), 200 µL 0.1 M DTT, 200 µL 0.65 mM hispidin aqueous solution with 0.1% formic acid and 0.1% Triton X-100, 5 ml of ~35 kDa fraction, 1 mL 10 mM NADPH aqueous solution.

Figure 10:
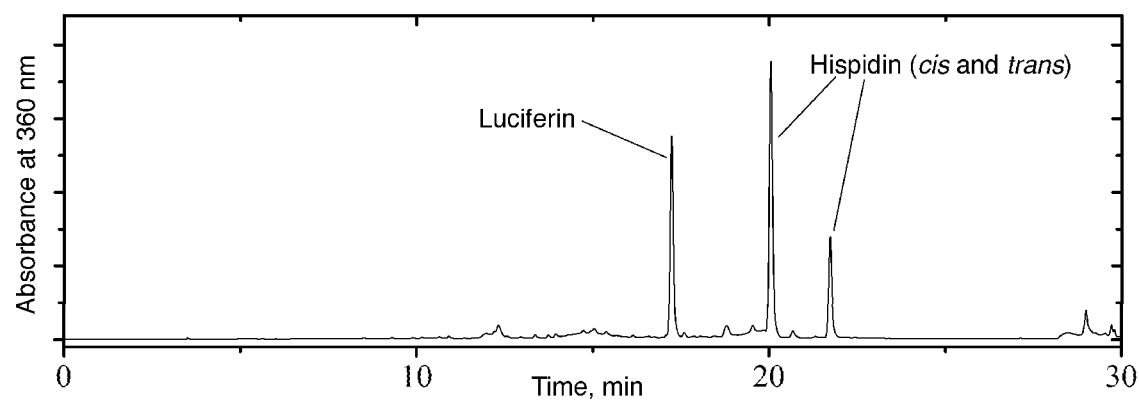
FIG. 10 shows the results of HPLC of the reaction mixture demonstrating NADPH-independent luminescence.

1 µL reaction mixture aliquots were added to the microsomal fraction of the cold extract of *N. nambi* every 5 minutes, and NADPH-independent luminescence of luciferase with a substrate thereof (luciferin) was observed. HPLC analysis showed that after initiation of the incubation at room temperature, a new compound, whose concentration reached maximum after 35 minutes of incubation, was produced and accumulated in the reaction mixture (FIG. 10).

The reaction was terminated by acidification to pH 2.0 by adding 150 µL of concentrated hydrochloric acid, centrifuged at 30000 G for 15 minutes and concentrated using the columns of Diapak-S16 (BioChemMak S&T, Russia). The columns were washed with 10 mM HCl containing 3% MeCN and eluted with 2 mL 75% MeCN aqueous solution. The eluate was concentrated to the volume of 50 µL by vacuum centrifugation. The obtained solution was dissolved in 50 µL of DMSO and used for reversed-phase chromatography using a semi-preparative column ZORBAX Eclipse XDB-$C_{18}$ (9.4 mm×250 mm, Agilent, USA). 0.1% formic acid (pH 2.8) was used as solvent A, and acetonitrile was used as solvent B. The gradient program of 5-40% solvent B was used for 25 minutes. The chromatography temperature was 25° C., the flow rate was 3 mL/min. Absorption was registered at 210, 230, 250, 270, 290, 310, 330 and 360 nm. The peak which appeared after 17.2 minutes of chromatography was collected. As a result, 19 µg of luciferin was produced from 32 µg of hispidin.

Figure 11:
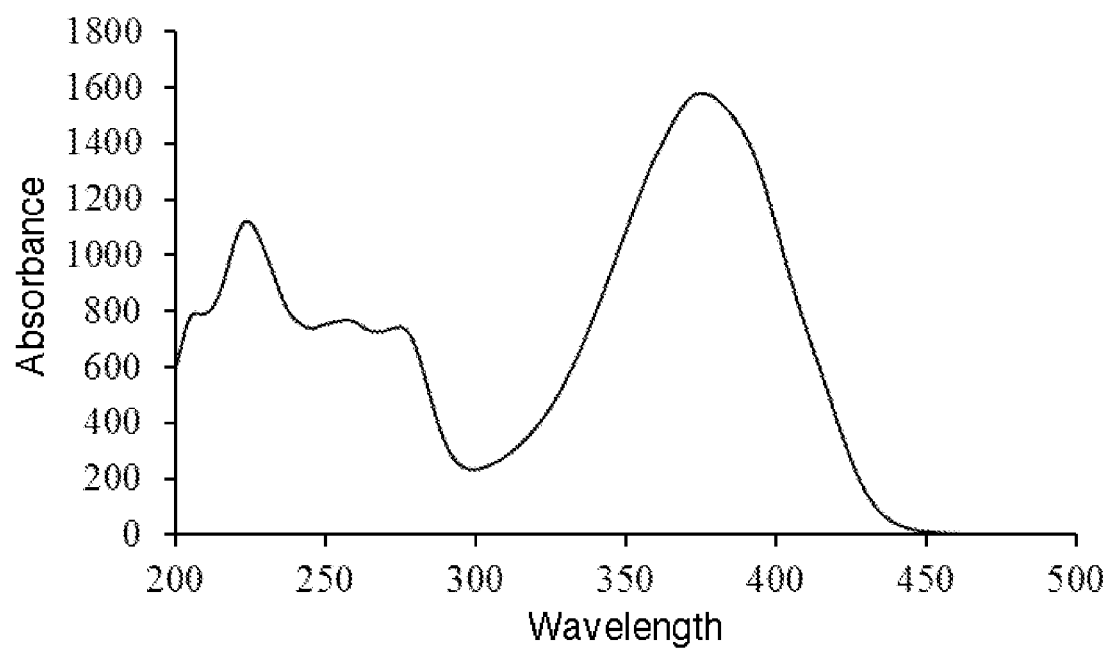
FIG. 11 shows UV-vis spectrum of luciferin isolated from the reaction mixture demonstrating NADPH-independent luminescence.
Figure 12:
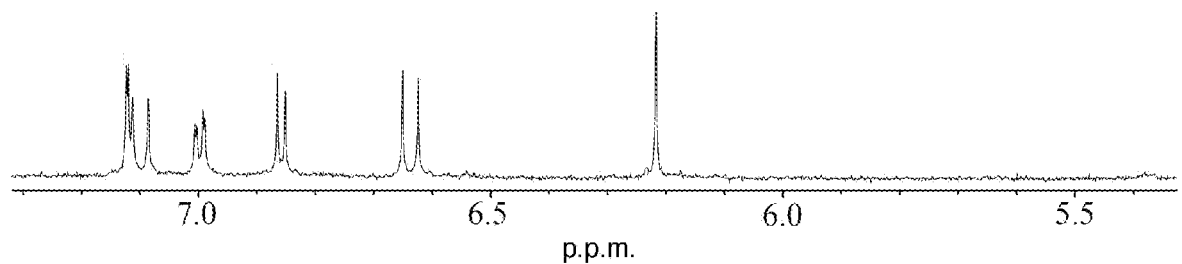
FIG. 12 shows $^1$H NMR spectrum of luciferin isolated from the reaction mixture demonstrating NADPH-independent luminescence (ppm—.part per million).

The UV-vis spectrum of the isolated luciferin was substantially identical to that of hispidin (FIG. 11), $^1$H NMR spectrum showed an identical pattern of protons in luciferin and hispidin; however, there was no signal corresponding to hispidin H-3 (FIG. 12). HRMS of luciferin showed the presence of a molecular ion with mass-to-charge (m/z) ratio of 263.0572 corresponding to the empirical formula of $C_{13}H_{11}O_6^+$ (the calculated m/z is 263.0550). This made it possible to unambiguously identify the isolated luciferin as 3-hydroxylated hispidin, the structure of which is shown in FIG. 1, to determine the nature of NADPH-dependent reaction of luciferin synthesis from hispidin as hydroxylation, and to determine the nature of NADPH-dependent enzyme of the fungal bioluminescent system as hispidin-3-hydroxylase.

Example 4

Using 3-hydroxyhispidin for Detecting Luciferase in Biological Samples 3-hydroxyhispidin was obtained as described in Example 3. The microsomal fractions of the cold extracts of *Neonothopanus nambi, Mycena citricolor, Panellus stipticus* and *Armillaria borealis* were used as biological samples. The cold extracts were obtained as described in Example 2. The microsomal fractions were obtained as described in Example 3.

10 μg of 3-hydroxyhispidin were dissolved in 1 mL 50% water-acetonitrile mixture containing 0.1% formic acid.

During the experiment, in each case, the background luminescence of the microsomal fraction was measured in the first place, and then, at 0.7 and 1.55 minutes, 3-hydroxyhispidin solution aliquots were added, which contained 0.006 ng and 0.16 ng of luciferin, correspondingly.

Figure 13:
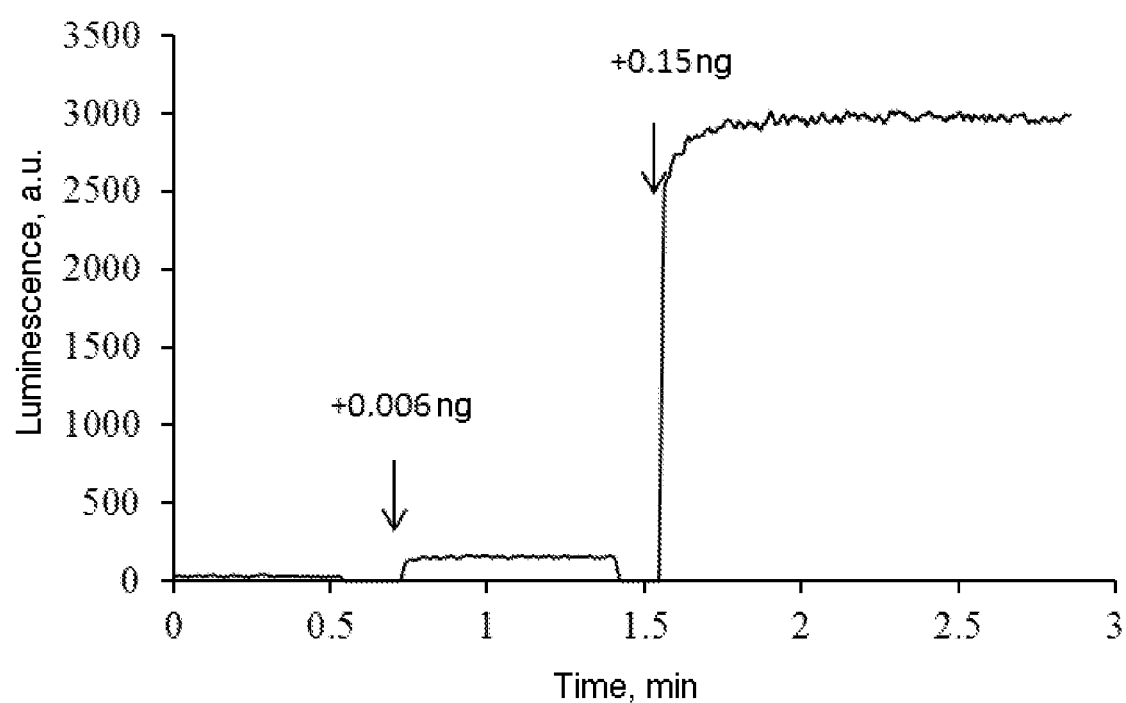
FIG. 13 shows a typical result of detection of luminescence of biological samples from fungi after adding 3-hydroxyhispidin.

In all cases, biological sample luminescence was detected; the typical result is shown in FIG. 13.

Example 5

Using Hispidin for Detecting Luciferase and hispidin-3-hydroxylase in Biological Samples Commercially available hispidin (Sigma-Aldrich, USA) was used for detecting luciferase and hispidin-3-hydroxylase in the cold extracts obtained from the mycelia of Neonothopanus nambi, Mycena citricolor, Panellus stipticus, and Armillaria borealis as described in Example 1.

Hispidin was dissolved in DMSO to a final concentration of 8 mg/ml (32 mM). Then, the obtained concentrated solution was diluted 500-fold by aqueous solution containing 0.1% Triton X-100 and 0.1% formic acid. Hispidin concentration in the obtained working solution was 64 μM.

The reaction mixture in Glomax 20/20 cuvette (Promega, USA) comprised: 100 μL 0.2 M phosphate buffer, pH 7.5, comprising 0.1 mM DTT and 0.1 mM EDTA, 1-5 μL of fungal extract, 4 μL 64 μM hispidin solution. The luminescent reaction was initiated by adding 4 μL 10 mM NADPH. Until adding NADPH, the reaction mixture did not produce detectable luminescence.

Figure 14:
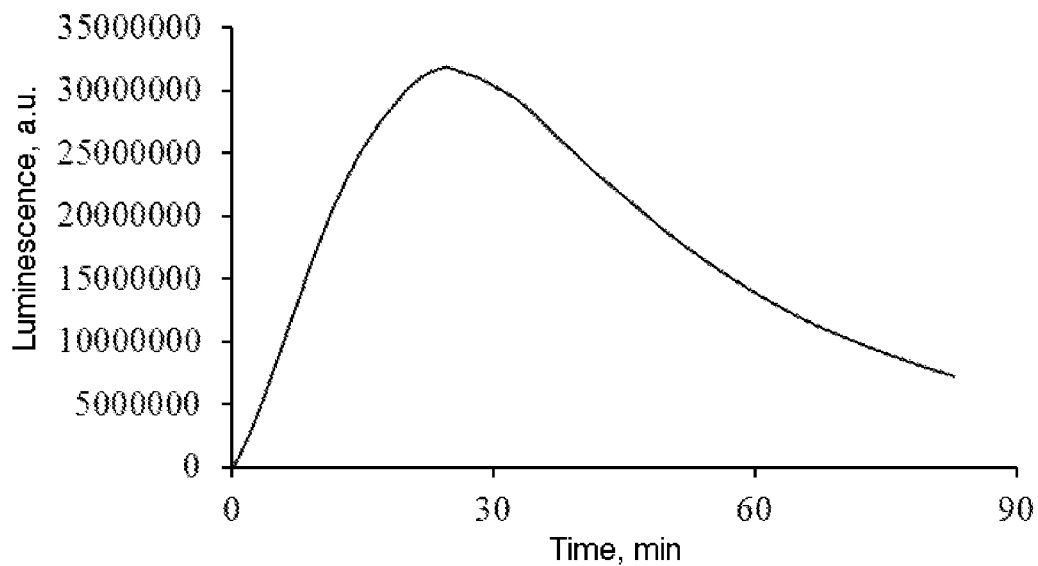
FIG. 14 shows a typical result of detection of luminescence of biological samples from fungi after adding hispidin and NADPH.

Luminescence was detected in all cases, its intensity reached maximum value (Imax) in 5 to 30 minutes after reaction initiation. The typical result of the experiment is shown in FIG. 14.

In a different experiment, the same samples were tested for the presence of luciferase and hispidin-3-hydroxylase activities as described above with the exception that NADH was used (instead of NADPH). In this case, luminescence was 2-3 times lower than when using NADPH.

The effect of hispidin concentration on the efficiency of luminescence of the biological samples was studied.

The concentrated hispidin solution was used to produce dilutions of 1/50, 1/500, 1/5000, 1/50000 in an aqueous solution with 0.1% Triton X-100 and 0.1% formic acid.

Figure 15:
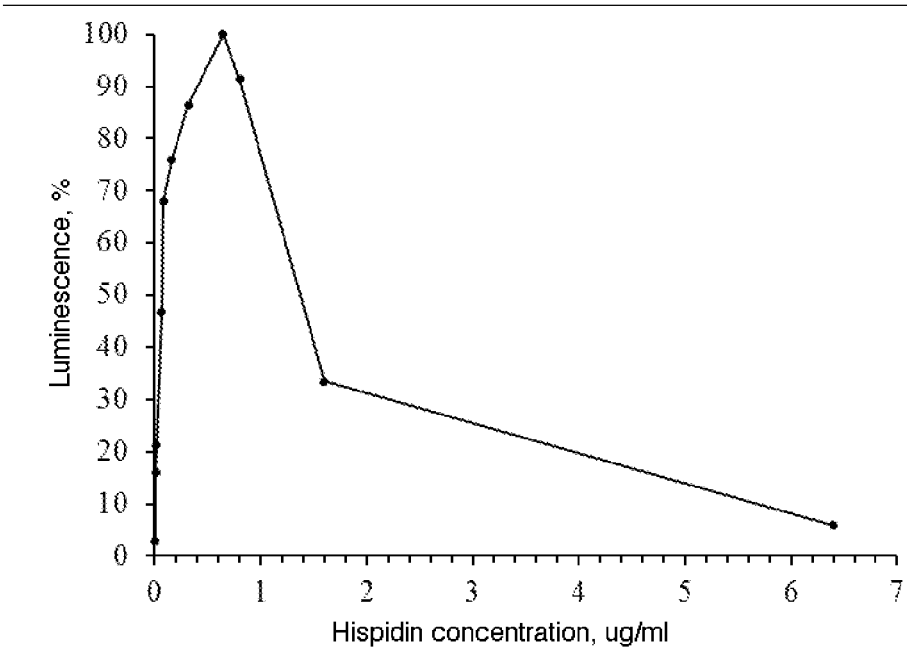
FIG. 15 shows the dependence of the maximal bioluminescence of a biological sample on a concentration of hispidin in the reaction mixture.

The reaction mixture in the bioluminometer cuvette comprised: 100 μL 0.1 M phosphate buffer, pH 7.5, containing 0.1 mM DTT, 4 μL of the cold extract of N. nambi, 1-5 μL of hispidin dilutions. The bioluminescent reaction was activated by adding 4 μL 10 mM NADPH. Bioluminescence was measured at 25° C. FIG. 15 shows the dependence of the maximum bioluminescence of the sample from hispidin concentration in the reaction mixture. The optimal hispidin concentration in the reaction mixture is 2.5 μM; detectable luminescence was observed when the reaction mixture contained hispidin at a concentration of 0.002 μM and more, and at a concentration of hispidin of more than 5 μM the inhibition of the luminescent reaction was observed, which was probably connected with substrate inhibition.

The effect of detergent concentration on the efficiency of luminescence of the biological samples was studied.

Figure 16:
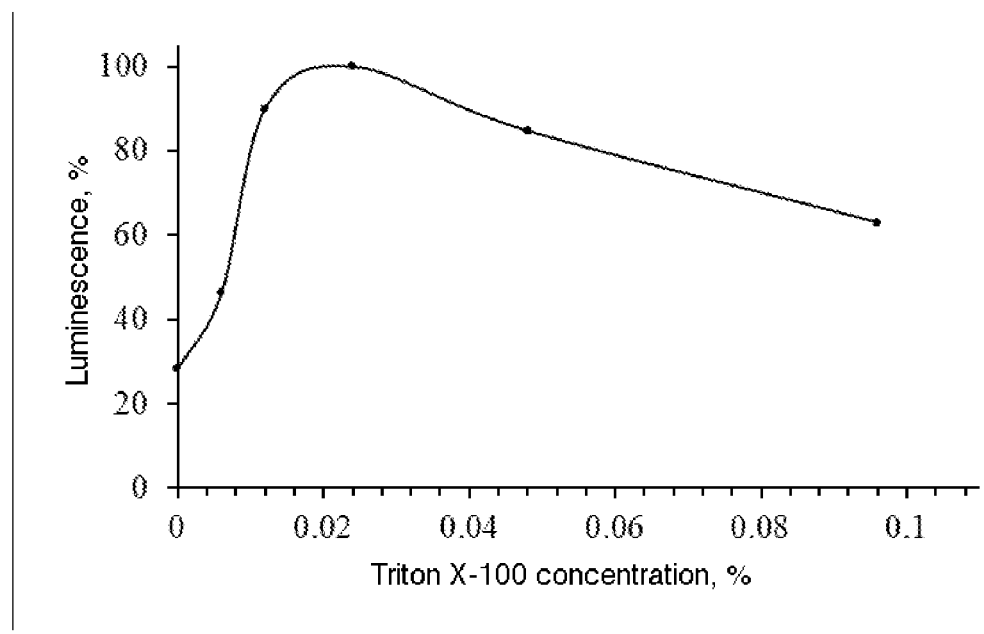
FIG. 16 shows the dependence of the maximal bioluminescence of a biological sample on a concentration of Triton X-100 detergent in the reaction mixture.

The reaction mixture in the bioluminometer cuvette comprised: 100 μL 0.1 M phosphate buffer, pH 7.5, comprising 0.1 mM DTT, 4 μL of the cold extract of N. nambi, 4 μL 64 μM hispidin solution and various amounts of Triton X-100 detergent. The bioluminescent reaction was activated by adding 4 μL 10 mM NADPH. FIG. 16 shows Imax dependence on detergent concentration. The optimal detergent concentration in the reaction mixture was determined as 0.015 to 0.03%. The maximum detergent concentration at which bioluminescence was observed was 0.5%.

The effect of molar concentration of the buffer solution on the efficiency of luminescence of the biological samples was studied.

Figure 17:
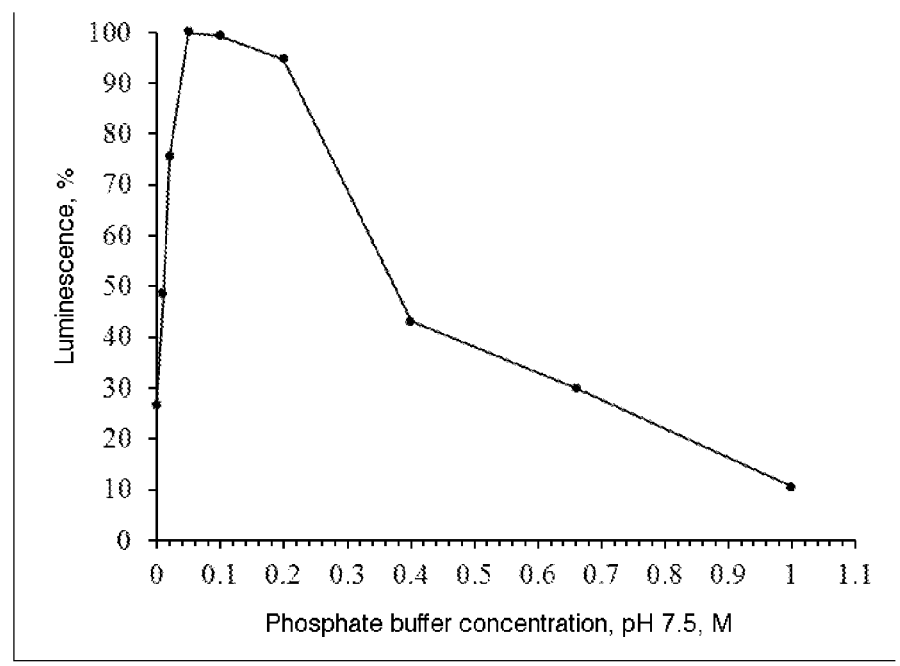
FIG. 17 shows the dependence of the maximal bioluminescence of a biological sample on the concentration of the buffercomponents in the reaction mixture.

The reaction mixture in the bioluminometer cuvette comprised: 100 μL of phosphate buffer of various molar concentrations, pH 7.5, comprising 0.1 mM DTT, 4 μL of the cold extract of N. nambi, 4 μL 64 μM hispidin solution. The bioluminescent reaction was activated by adding 4 μL 10 mM NADPH. Bioluminescence was measured at 25° C. FIG. 17 shows Imax dependence on a molar concentration of the buffer solution. In this experiment, the optimal molar concentration of the buffer solution was 0.05 to 0.2 M. Detectable bioluminescence is observed at 1 mM and lower; luminescence intensity in water, without adding a buffer, was 25% of the maximum value.

The effect of pH of the buffer solution on the efficiency of luminescence of the biological samples was studied. The reaction was implemented as described above using 0.1 M Tris HCl and a phosphate buffer. According to the data obtained, luminescence of the biological sample can be detected within the pH range of 6.0 to 9.8; optimally, the pH of buffer solutions should be within the range of 7.0 to 9.5.

The effect of NADPH concentration on the efficiency of luminescence of the biological samples was studied.

Figure 18:
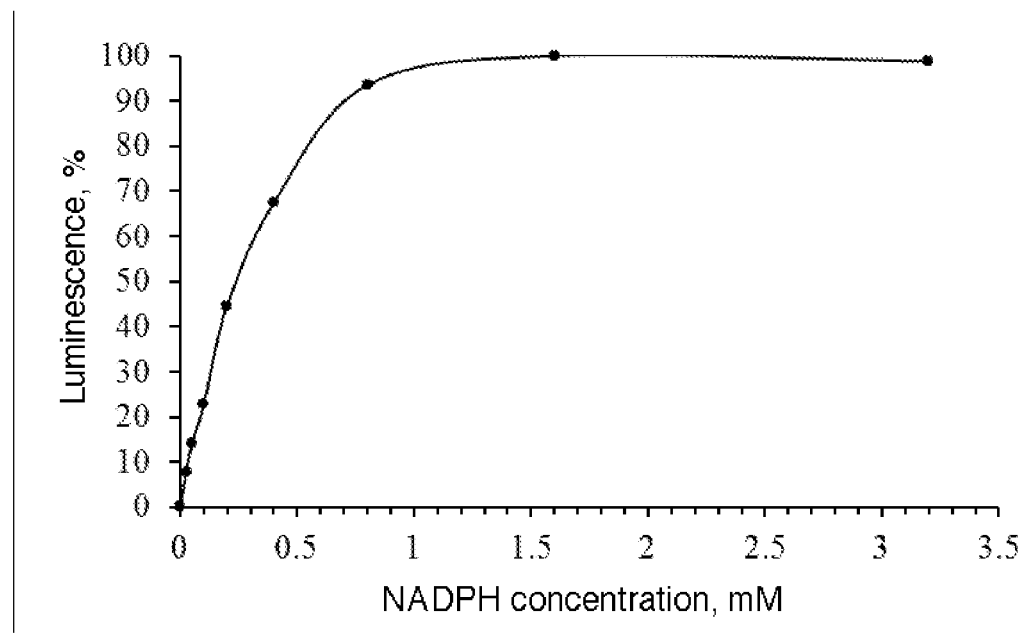
FIG. 18 shows the dependence of the maximal bioluminescence of a biological sample on the concentration of NADPH in the reaction mixture.

The reaction mixture in the bioluminometer cuvette comprised: 100 μL 0.1 M phosphate buffer, pH 7.5, comprising 0.1 mM DTT, 4 μL of the cold extract of N. nambi, 4 μL 64 mM hispidin solution. The bioluminescent reaction was activated by adding various amounts of NADPH. FIG. 18 shows Imax dependence on NADPH concentration. The minimum NADPH concentration which provided detectable bioluminescence was 20 μM.

The effect of DTT concentration on the efficiency of luminescence of the biological samples was studied.

Figure 19:
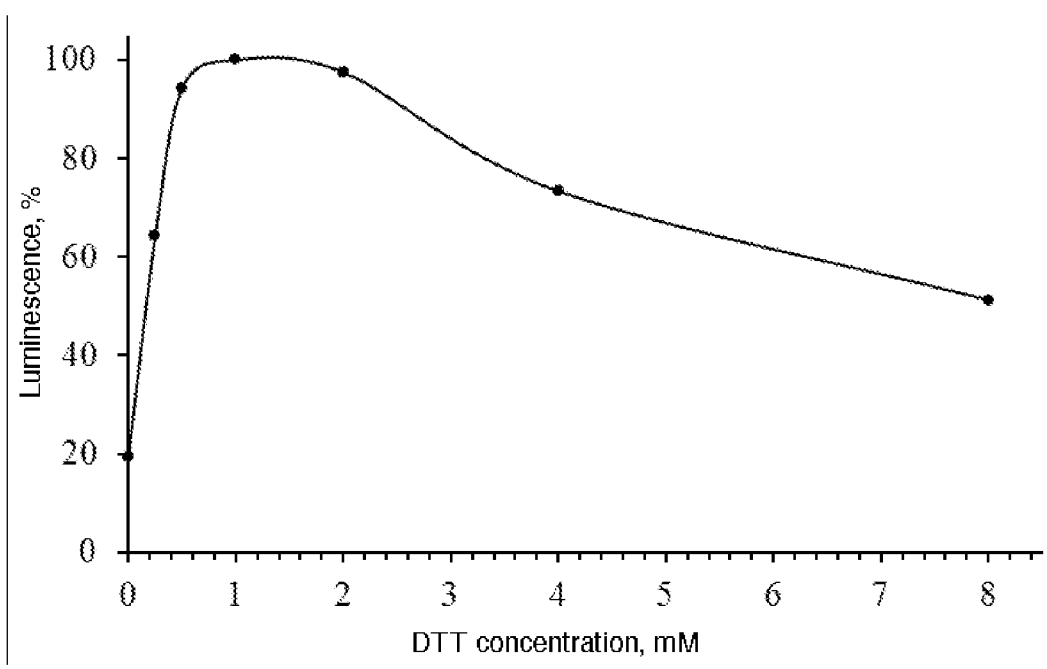
FIG. 19 shows the dependence of the maximal bioluminescence of a biological sample on a concentration of DTT in the reaction mixture.

The reaction mixture in the bioluminometer cuvette comprised: 100 μL 0.1 M phosphate buffer, pH 7.5, comprising various concentrations of DTT, 4 μL of the cold extract of N. nambi, 4 μL 64 μM hispidin solution. The bioluminescent reaction was activated by adding 4 μL 10 mM NADPH. FIG. 19 shows Imax dependence on DTT concentration. The optimal DTT concentration in the reaction mixture was 0.5 to 3 mM. The maximum DTT concentration which provided bioluminescence was 10 mM.

What is claimed is:

1. A method for detecting fungal luciferase in a biological sample comprising
   a) adding 3-hydroxyhispidin or 3-hydroxybisnoryangonin to the biological sample to form a reaction mixture;
   b) incubating the reaction mixture under conditions which allow for bioluminescence;
   c) detecting bioluminescence of the reaction mixture.

2. A method for detecting fungal luciferase in the presence of hispidin-3-hydroxylase in a biological sample comprising
   a) adding hispidin or bisnoryangonin and NAD(P)H to the biological sample to form a reaction mixture;
   b) incubating the reaction mixture under conditions which allow for bioluminescence;
   c) detecting bioluminescence of the reaction mixture.

3. The method of claim 1, wherein the fungal luciferase comprises recombinant luciferase.

4. The method of claim 1, wherein the biological sample comprises tissue or a cell.

5. The method of claim 2, wherein the fungal luciferase comprises recombinant luciferase.

6. The method of claim 2, wherein the biological sample comprises tissue or a cell.

7. A method for detecting bioluminescence in a biological sample comprising
   a) expressing a recombinant fungal luciferase in the biological sample;
   b) adding 3-hydroxyhispidin or 3-hydroxybisnoryangonin to the biological sample; and
   c) detecting bioluminescence.

8. The method of claim 7, wherein the 3-hydroxyhispidin or 3-hydroxybisnoryangonin is added to the biological sample to a final concentration of 0.03 to 30 μM, and the biological sample has a pH in the range of 6.0 to 9.8.

9. The method of claim 7, wherein the fungal luciferase is a functional mutant.

10. The method of claim 7, wherein the biological sample does not comprise a tissue, a cell, an extract, a homogenate, or a protein, obtained from a fungus.

11. The method of claim 7, wherein the biological sample comprises tissue or a cell.

* * * * *